United States Patent [19]
Holmes et al.

[11] Patent Number: 5,618,308
[45] Date of Patent: *Apr. 8, 1997

[54] SURGICAL INSTRUMENT CAPABLE OF DISASSEMBLY

[75] Inventors: J. Stephen Holmes, Atlanta, Ga.; Charles E. Beuchat, Irvine, Calif.

[73] Assignee: Wright Medical Technology, Inc., Arlington, Tenn.

[ * ] Notice: The term of this patent shall not extend beyond the expiration date of Pat. No. 5,336,238.

[21] Appl. No.: 573,283

[22] Filed: Dec. 15, 1995

Related U.S. Application Data

[63] Continuation of Ser. No. 134,087, Oct. 8, 1993, Pat. No. 5,507,774, which is a continuation-in-part of Ser. No. 93,477, Jul. 19, 1993, Pat. No. 5,336,238.

[51] Int. Cl.$^6$ ................................... A61B 17/28
[52] U.S. Cl. .................... 606/205; 606/170; 606/208
[58] Field of Search ...................... 606/205, 206, 606/207, 208, 51, 52, 170, 174; 128/751; 81/416

[56] References Cited

U.S. PATENT DOCUMENTS

| | | |
|---|---|---|
| 1,510,416 | 9/1924 | Pietz et al. ...................... 606/208 X |
| 2,113,246 | 4/1938 | Wappler . |
| 3,735,763 | 5/1973 | Shannon et al. ...................... 606/208 |
| 3,870,048 | 3/1975 | Yoon . |
| 3,964,468 | 6/1976 | Schulz . |
| 4,085,743 | 4/1978 | Yoon . |
| 4,369,788 | 1/1983 | Goald . |
| 4,427,014 | 1/1984 | Bel et al. . |
| 4,569,131 | 2/1986 | Falk et al. . |
| 4,760,848 | 8/1988 | Hasson . |
| 4,763,668 | 8/1988 | Macek et al. . |
| 4,962,770 | 10/1990 | Agee et al. . |
| 4,982,727 | 1/1991 | Sato . |
| 5,133,735 | 7/1992 | Slater et al. . |
| 5,133,736 | 7/1992 | Bales, Jr. et al. . |
| 5,188,494 | 2/1993 | Hatin ...................... 411/157 X |
| 5,325,866 | 7/1994 | Krzyzanowski ...................... 128/751 |

*Primary Examiner*—Michael H. Thaler
*Attorney, Agent, or Firm*—Walker, McKenzie & Walker, P.C.

[57] ABSTRACT

A surgical instrument which easily disassembles for sterilization comprises an inner rod coaxially disposed in a hollow tube with a handle at one end of the rod and a working tip at the other end. The handle is detachably interconnected to the inner rod and the inner rod is detachably interconnected to the hollow tube by the cooperation of at least one locking pin secured to the inner rod and a locking tab formed on the inner surface of the hollow tube.

8 Claims, 4 Drawing Sheets

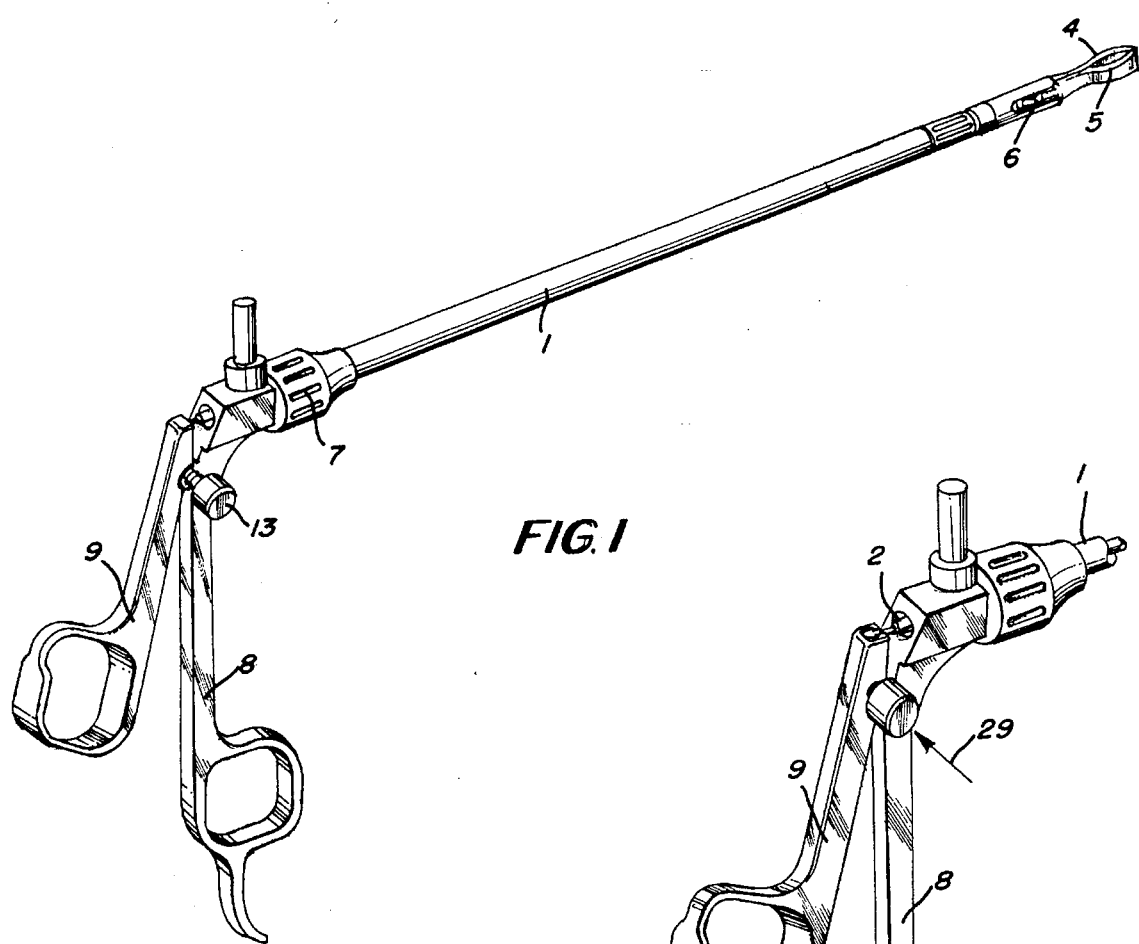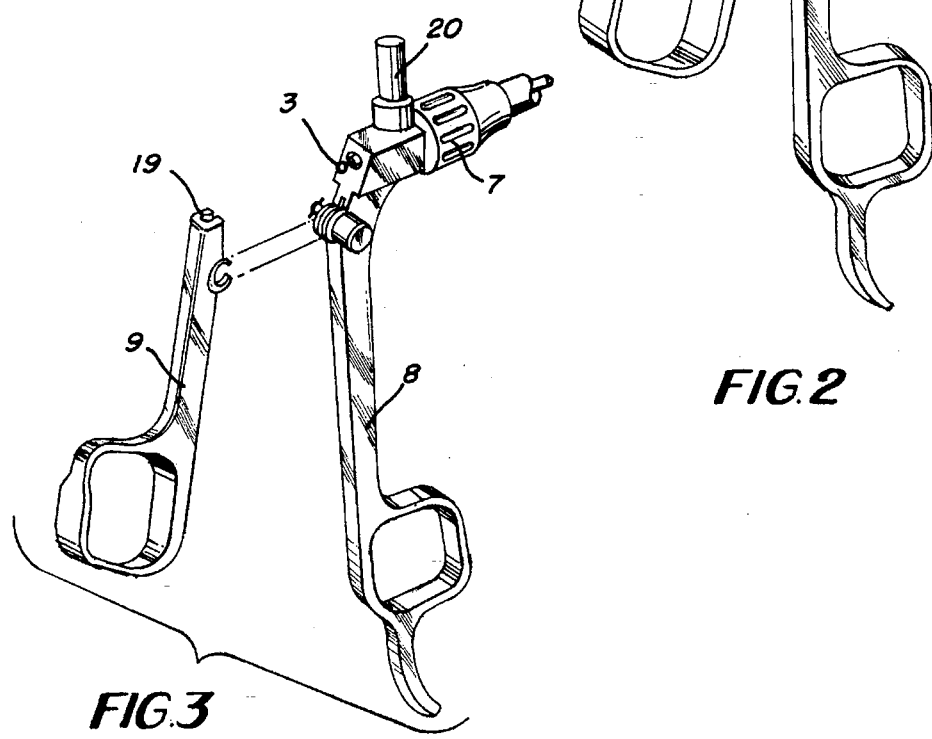

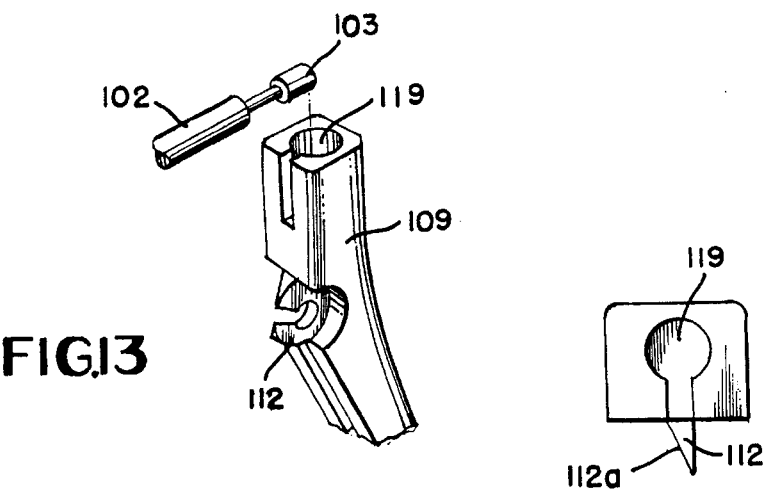
FIG.13
FIG.15
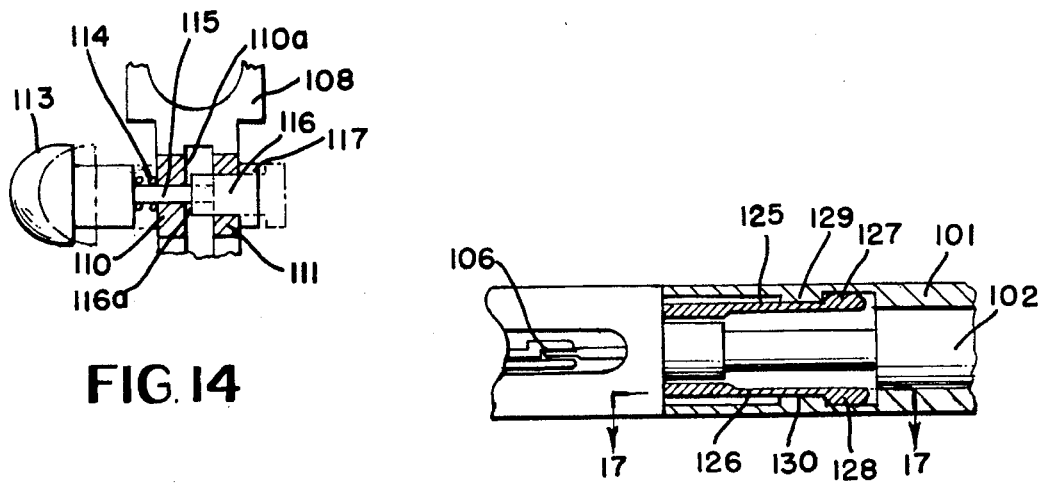
FIG.14
FIG.16
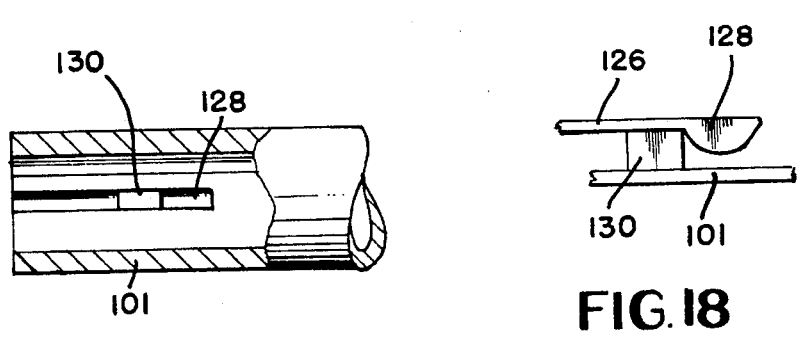
FIG.17
FIG.18

SURGICAL INSTRUMENT CAPABLE OF DISASSEMBLY

CROSS REFERENCE TO RELATED APPLICATIONS

This is a continuation of U.S. application Ser. No. 08/134,087 filed on Oct. 8, 1993, now U.S. Pat. No. 5,507,774 entitled "SURGICAL INSTRUMENT CAPABLE OF DISASSEMBLY," which is a continuation-in-part of U.S. application Ser. No. 08/093,477 filed on Jul. 19, 1993, now U.S. Pat. No. 5,336,238, entitled "SURGICAL INSTRUMENT CAPABLE OF DISASSEMBLY."

BACKGROUND OF THE INVENTION

Up until recently, most abdominal and thoracic procedures required major incisions in order to provide an ability to observe the body cavity and perform any necessary diagnosis and treatment. This invention relates generally to surgical instruments for use in minimally invasive surgical procedures. In general, instruments used in these procedures are of the closed shaft variety. Since these instruments usually cannot be disassembled, complete sterilization is not possible because microscopic pockets of tissue and blood are often left on the instrument even after completion of accepted sterilization procedures.

In order to insure complete sterilization of a closed shaft surgical instrument, the instrument must essentially be capable of disassembly into its major components so that the resulting openings are of sufficient magnitude to accept cleaning brushes. This insures that all surfaces of the instrument are exposed to the particular sterilization medium and any concern that the instrument is not thoroughly sterilized is thereby eliminated.

SUMMARY OF THE INVENTION

By this invention, a surgical instrument is provided and comprises an inner rod coaxially disposed within a hollow tube and which has a working tip at the distal end and a handle at the proximal end and wherein the handle is detachably interconnected to the inner rod. Also, at least one locking pin is secured to the distal end of the inner rod and is capable of being interlocked with a locking tab formed on the inner surface of the hollow tube.

BRIEF DESCRIPTION OF THE DRAWINGS

In the drawings,

FIG. 1 is a perspective view of a surgical instrument capable of disassembly according to this invention;

FIG. 2 is a perspective view of the instrument handle;

FIG. 3 is a perspective view of the handle in disassembled condition;

FIG. 13 is a perspective view of the alternative means for interconnecting the handle and the inner rod;

FIG. 14 is a cross-sectional view of the alternative handle release means;

FIG. 15 is an enlarged cross-sectional view of a portion of the alternative means for interconnecting the handle and the inner rod;

FIG. 16 is a cross-sectional view of the alternative means for interconnecting the outer hollow tube and the inner rod;

FIG. 17 is a view taken along the line 17—17 in FIG. 16; and

FIG. 18 is an enlarged cross-sectional view of the alternative locking pin and locking tab.

DESCRIPTION OF THE PREFERRED EMBODIMENTS

Figure 4:
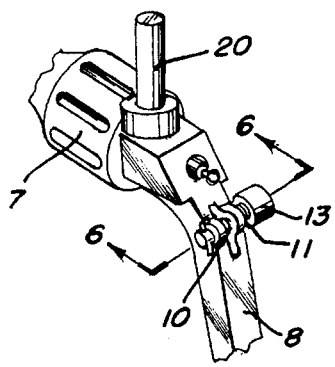
FIG. 4 is a perspective view of the handle release means.

In the drawings, the numeral 1 designates the outer hollow tube of the surgical instrument and the numeral 2 identifies the inner rod which has locking element 3 disposed at one end thereof. The working tip of the instrument is disposed at the distal end thereof and comprises jaws 4 and 5 which are opened and closed by means of linkage mechanism 6, as is well known.

Disposed at the proximal end of the instrument and secured to hollow tube 1 is rotation knob 7. In order to facilitate a 360 degree rotation of jaws 4 and 5, rotation knob 7 is pivotally mounted on handle element 8.

Figure 6:
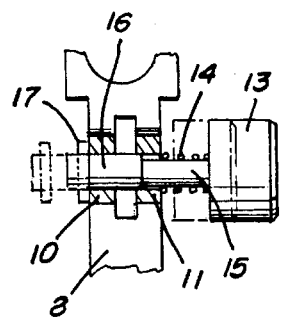
FIG. 6 is a cross-sectional view taken along the line 6—6 in FIG. 4.

Handle element 9 is detachably connected to handle element 8 by locking means best shown in FIG. 6. More specifically, the locking means comprises closed rings 10 and 11 integrally formed on handle element 8 and partially closed ring 12 integrally formed on handle element 9. Knob 13 is biased outwardly of the handle means or to the right, as viewed in FIG. 6, by means of compression spring 14. Of course, knob 13 would also be operable if disposed on the opposite side of the handle means. Attached to knob 13 is a locking rod which comprises an inner portion 15 which is of smaller diameter than associated outer portion 16. Retaining pin 17 is secured on the end of the locking rod remote from knob 13 and acts to prevent the locking rod from disengagement from the instrument handle means.

Figure 5:
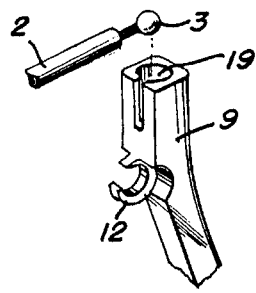
FIG. 5 is a perspective view of the means for interconnecting the handle and the inner rod.

As best shown in FIG. 5, means is provided to interconnect inner rod 2 and handle element 9. Specifically, inner rod 2 extends through aperture 18 of handle element 8 and forms an operably interconnected relationship with respect to handle element 9 by the interlocked disposition of locking element 3 being disposed in slot 19. Of course, operation of handles 8 and 9, in known manner, results in the activation of linkage mechanism 6 thereby causing jaws 4 and 5 to open and close as desired.

As is well known, monopolar post 20 is formed on the upper surface of handle element 8 at the proximal end of the instrument. Also, in order to improve the comfort and operability of the instrument, the handle itself is made of an ergonomic configuration.

Figure 9:
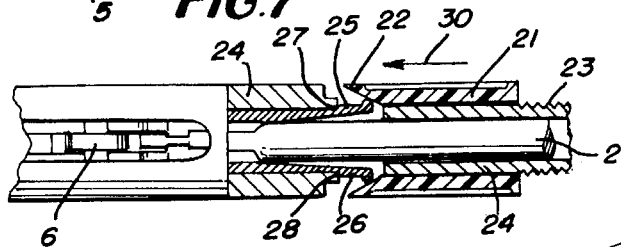
FIG. 9 is a cross-sectional view taken along the line 9—9 in FIG. 7.

According to this invention, inner rod 2 and the associated working tip of the instrument are disjointably connected to hollow tube 1 by means of a collet mechanism. Specifically, collet 21 is rotatable about inner rod 2 independently of hollow tube 1 and comprises bevelled surface 22 at one end thereof. Externally threaded end 23 of attachment housing 24 is engageable with internal threads formed on the distal end of hollow tube 1. As best shown in FIG. 9, locking pins 25 and 26 are attached to the housing for linking mechanism 6 in a spring-like fashion and are provided, respectively, with notches 27 and 28. In the assembled instrument, locking pins 25 and 26 are disposed in slotted openings formed in attachment housing 24 such that notches 27 and 28 engage attachment housing 24.

Figure 10:
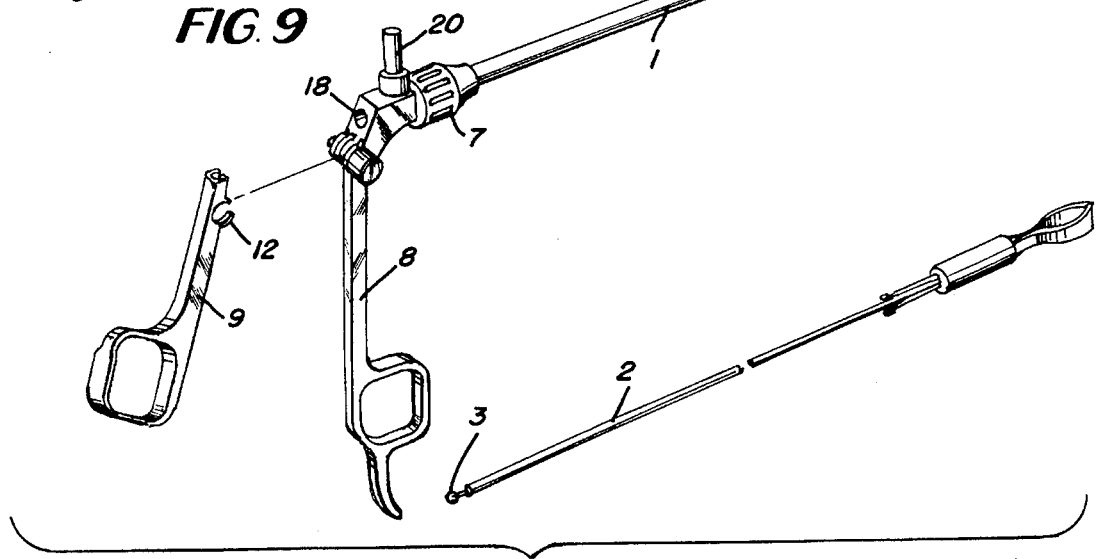
FIG. 10 is a perspective view of the instrument in disassembled condition.

In order to disassemble the fully assembled instrument, as shown in FIG. 1, into the fully disassembled instrument, as shown in FIG. 10, initially knob 13 is pushed inwardly of the handle as indicated by arrow 29 in FIG. 2. This causes the smaller diameter portion 15 of the locking rod to move to the left, as viewed in FIG. 6, thus allowing the open segment of ring 12 to slip past portion 15 which results in the separation of handle elements 8 and 9. Simultaneously with the separation of handle elements 8 and 9, locking element 3 is maneuvered out of slot 19, as best viewed in FIG. 5.

Following this operation, collet 21 is manually pushed toward the distal end of the instrument, as indicated by arrow 30 in FIG. 9, so as to cause the ends of locking pins 25 and 26 to slide along bevelled surface 22 of collet 21 thereby compressing locking pins 25 and 26 inwardly with respect to inner rod 2 a sufficient distance to allow notches 27 and 28 to disengage attachment housing 24. Inner rod 2 and the associated working tip of the instrument can then be easily disassembled whereby locking element 3 is withdrawn initially through aperture 18 and then inner rod 2 is pulled all the way through hollow tube 1. The instrument is then disposed in a disassembled condition as shown in FIG. 10.

Following disassembly, the individual elements of the instrument are conveniently and thoroughly sterilized by means of accepted sterilization procedures. The instrument is then reassembled by inserting inner rod 2 through hollow tube 1 and aperture 18 wherein locking element 3 is simply inserted into slot 19. Knob 13 is then depressed thereby allowing ring 12 to be positioned around portion 15 of the locking rod. Simultaneously with this operation, locking pins 25 and 26 are interlocked with attachment housing 24 respectively by means of notches 27 and 28. When knob 13 is released, outer portion 16 enters ring 12 and is of sufficiently large diameter to prevent disengagement from the open segment of ring 12 so as to secure the handle in a completely assembled condition whereby the instrument is ready for reuse in an appropriate surgical procedure.

Figure 11:
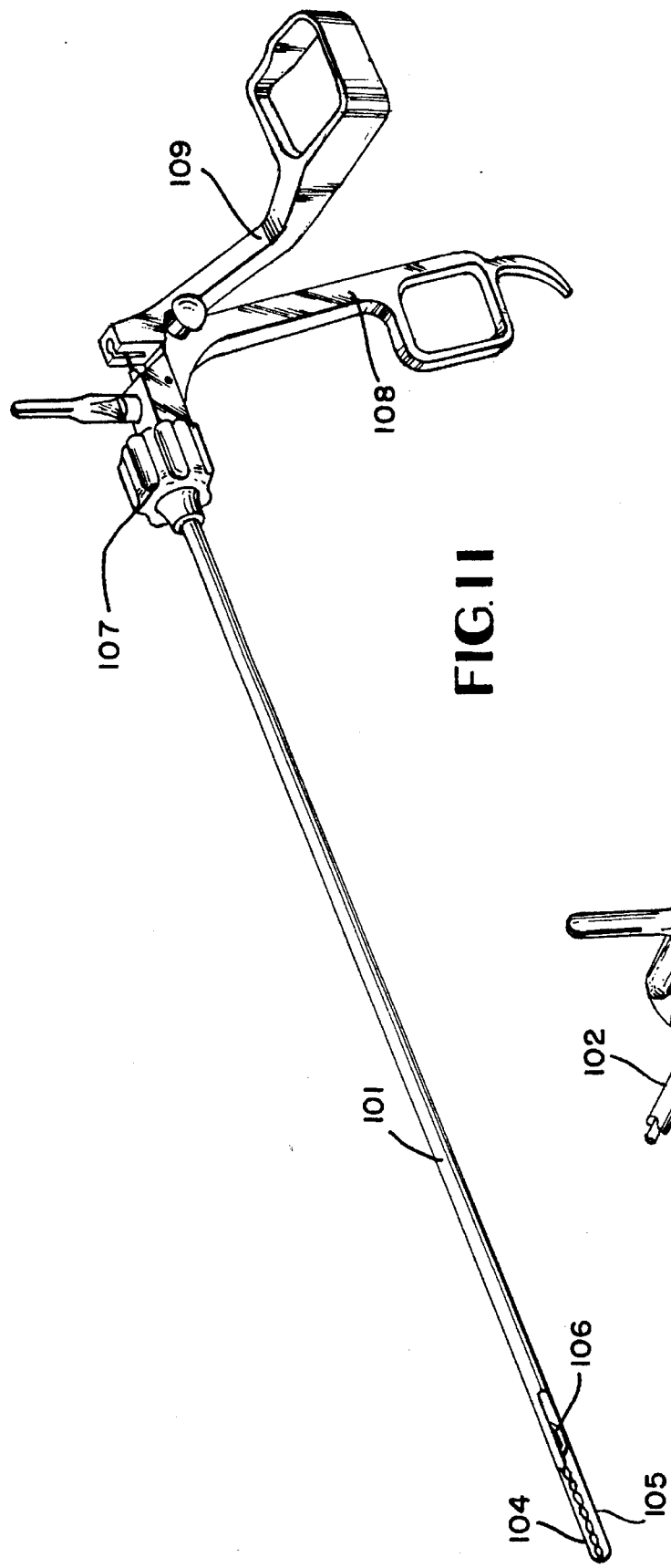
FIG. 11 is a perspective view of an alternative embodiment of the instrument.
Figure 12:
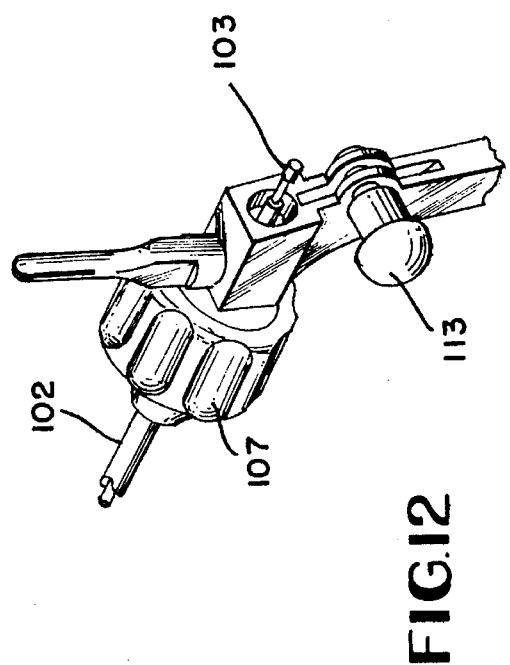
FIG. 12 is a perspective view of the alternative handle release means.

FIGS. 11–18 depict an alternative embodiment of the surgical instrument shown in FIGS. 1–10. With particular reference to FIGS. 11 and 12, the numeral 101 designates the outer hollow tube of the surgical instrument and the numeral 102 identifies the inner rod which has locking element 103 disposed at one end thereof. The working tip of the instrument is disposed at the distal end thereof and comprises jaws 104 and 105 which are opened and closed by means of linkage mechanism 106. Disposed at the proximal end of the instrument and secured to hollow tube 101 is rotation knob 107. Handle elements 108 and 109 are provided and are interconnected by locking means best shown in FIGS. 13–15. Also, handle element 109 is offset approximately 30 degrees in order to improve the comfort and operability of the instrument.

Handle locking means for the alternative embodiment of the instrument comprises closed rings 110 and 111 which are integrally formed on handle element 108 together with partially closed ring 112 integrally formed on handle element 109. Knob 113 is biased outwardly of the handle means or to the left, as viewed in FIG. 14, by means of compression spring 114. As discussed in connection with knob 13, knob 113 would also be operable if disposed on the opposite side of the handle means. Attached to knob 113 is a locking rod which comprises an inner portion 115 which is of smaller diameter than associated outer portion 116. Retaining pin 117 is secured on the end of the locking rod remote from knob 113 and acts to prevent disengagement of the locking rod from the instrument handle means. According to the alternative embodiment of this invention, ring 112 is provided with bevelled surface 112a as best viewed in FIG. 15.

Figure 7:
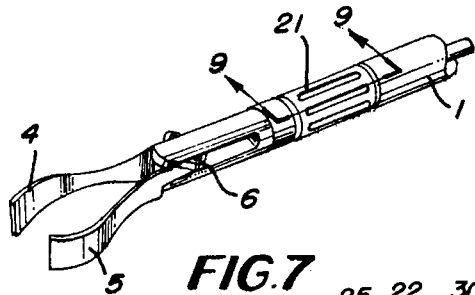
FIGS. 7 and 8 are perspective views of the distal end of the instrument.
Figure 8:
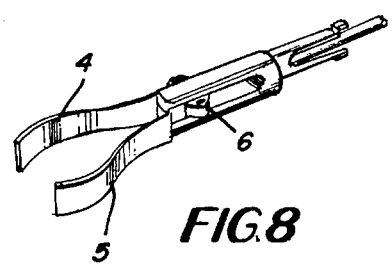

Also according to the alternative embodiment of the invention, inner rod 102 and the associated working tip of the instrument are disjointably connected to hollow tube 101 by means similar to that shown and described in connection with FIGS. 7–9. More specifically and as best shown in FIGS. 16–18, locking pins 125 and 126 are attached to the housing for linkage mechanism 106 in a spring-like fashion and are provided, respectively, with protuberances 127 and 128. It has been found that the optimum metallurgical compound for locking pins 125 and 126 is steel 420 heat treated. Protuberances 127 and 128 are shaped in a rounded configuration, as best shown in FIG. 18, in order to facilitate separation of hollow tube 101 and inner rod 102. Finally, locking tabs 129 and 130 are integrally formed on the inner surface of outer hollow tube 101.

In order to assemble the instrument depicted in FIGS. 11–18, inner rod 102 is slipped into hollow tube 101 and locking element 103 is inserted into slot 119. Then with handle element 108 and associated locking means disposed as shown in FIG. 14 and with inner surface 116a of enlarged portion 116 spaced from the adjacent surface 110a of closed ring 110, ring 112 is simply inserted into the gap between surfaces 110a and 116a. As ring 112 moves into position around smaller diameter portion 115 by means of its open segment, the locking rod is progressively forced to the right to an increasing degree by means of bevelled edge 112a. Then, when ring 112 is fully seated around the locking rod, larger diameter portion 116 is caused to move to the left by means of compression spring 114 causing ring 112 to snap into a locked disposition around outer portion 116. By this means, handle elements 108 and 109 are automatically locked together without having to manipulate knob 113.

Generally simultaneously with this operation, inner rod 102 is maneuvered into an Interlocked relation with outer hollow tube 101 by means of protuberances 127 and 128 of locking pins 125 and 126 which form an interlocked relationship, respectively, with locking tabs 129 and 130 integrally formed on the inner surface of outer hollow tube 101. The instrument is then disposed in a fully assembled operational condition as shown in FIG. 11.

In order to disassemble the fully assembled instrument, it is simply necessary to manually press knob 113 inwardly so as to allow ring 112 to disengage smaller diameter portion 115 of the locking rod through the open segment of ring 112 and simultaneously locking element 103 is removed from slot 119. Then the user must simply grasp the distal end of the instrument around the housing for linkage mechanism 106 such that pressure is applied to the instrument in an imaginary plane intersecting locking pins 125 and 126. Due to the spring-like nature of locking pins 125 and 126 and since the section of inner rod 102 adjacent locking pins 125 and 126 is of smaller diameter than the remainder of inner rod 102, this pressure will cause one of the locking pins to rotate inwardly toward the axis of inner rod 102. Since protuberances 127 and 128 are rounded, the locking pin which did not rotate into disengagement is easily caused to disengage its respective locking tab whereby inner rod 102 is then manually pulled outwardly through hollow tube 101.

Following disassembly, sterilization of the instrument components is undertaken. Then the alternative embodiment of the instrument is reassembled by inserting inner rod 102 into outer hollow tube 101. Locking element 103 is inserted into slot 119 and simultaneously locking pins 125 and 126 form an interlocked relationship with locking tabs 129 and 130, respectively, and ring 112 is automatically snapped into position around larger diameter portion 116 of the locking rod.

We claim:

1. A surgical instrument comprising a hollow tube having a longitudinal axis, an inner rod having proximal and distal ends and extending through said hollow tube, handle means for imparting reciprocal movement to said inner rod relative to said hollow tube, a working tip attached to said distal end, and means to detachably interconnect said hollow tube and said inner rod including a locking pin connected to said inner rod and a locking tab formed on the inner surface of said hollow tube such that said locking pin and said locking tab are capable of being interlocked and so that pressure applied to said instrument radially inward by grasping said instrument generally in an imaginary plane intersecting said locking pin and said locking tab will cause said locking pin to rotate inward and allow said inner rod to be pulled through said hollow tube to disconnect said distal end of said inner rod from said outer tube.

2. A surgical instrument according to claim 1 wherein said locking pin comprises a locking protuberance and wherein said locking protuberance engages said locking tab in an interlocked relationship.

3. A surgical instrument according to claim 2 wherein said locking protuberance is of a generally rounded configuration.

4. A surgical instrument according to claim 1 wherein said locking pin extends in a direction toward said proximal end.

5. A surgical instrument according to claim 1 wherein said working tip comprises a pair of jaws.

6. A surgical instrument according to claim 1 wherein said handle means is of ergonomic configuration.

7. A surgical instrument according to claim 1 wherein said locking pin includes an elongated finger having a first end secured relative to said distal end of said inner rod and having a second end extending in a direction toward said proximal end of said inner rod, said second end of said elongated finger having an outwardly directed protuberance for engaging said locking tab when said locking pin and said locking tab are interlocked; wherein said elongated finger of said locking pin has a spring-like nature; and wherein said inner rod has a section adjacent said second end of said elongated finger of smaller diameter than the remainder of said inner rod so that pressure applied to said instrument radially inward by grasping said instrument in an imaginary plane intersecting said protuberance of said second end of said elongated finger of said locking pin and said locking tab will cause said locking pin to rotate inward and allow said inner rod to be pulled from said hollow tube to disconnect said distal end of said inner rod from said hollow tube.

8. A surgical instrument comprising a hollow tube having a longitudinal axis, an inner rod having a longitudinal axis and having proximal and distal ends and extending through said hollow tube, handle means for imparting reciprocal movement to said inner rod relative to said hollow tube, a working tip attached to said distal end, and means to detachably interconnect said hollow tube and said inner rod including a locking pin connected to said inner rod and a locking tab formed on the inner surface of said hollow tube, said locking pin including a locking protuberance, said locking protuberance having a leading edge which passes over said locking tab during engagement of said inner rod and hollow tube, and a trailing edge which passes over said locking tab during disengagement, such that said locking pin and said locking tab are capable of being interlocked by way of said locking protuberance, wherein said trailing edge of said locking protuberance includes a convex rounded cam surface, whereby inward rotation of said locking pin leads to disengagement from said locking tab, said convex rounded cam surface being rounded in a cross-section taken along said longitudinal axis of said inner rod.

* * * * *